United States Patent
Wilson et al.

(10) Patent No.: US 7,563,400 B2
(45) Date of Patent: Jul. 21, 2009

(54) METHOD OF STENT MOUNTING TO FORM A BALLOON CATHETER HAVING IMPROVED RETENTION OF A DRUG DELIVERY STENT

(75) Inventors: Bruce Wilson, Temecula, CA (US); Christopher C. Andrews, Lake Elsinore, CA (US); Kenneth L. Wantink, Temecula, CA (US); Daniel G. Brown, Temecula, CA (US); Darrin J. Kent, Murrieta, CA (US); Jeremy L. Stigall, Murrieta, CA (US); Plaridel Kimpo Villareal, San Jose, CA (US); Shahin Sarkissian, San Jose, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 465 days.

(21) Appl. No.: 11/105,085

(22) Filed: Apr. 12, 2005

(65) Prior Publication Data
US 2006/0229712 A1 Oct. 12, 2006

(51) Int. Cl.
*B29C 65/02* (2006.01)
(52) U.S. Cl. .......................... 264/249; 264/512; 264/516
(58) Field of Classification Search ........................ None
See application file for complete search history.

(56) References Cited
U.S. PATENT DOCUMENTS

| | | | |
|---|---|---|---|
| 141,992 A | 8/1873 | Carr | |
| 430,928 A | 6/1890 | Doty | |
| 579,214 A | 3/1897 | Adams | |
| 696,289 A | 2/1902 | Williams | |
| 852,290 A | 4/1907 | Neal | |
| 915,184 A | 3/1909 | Keim | |
| 1,045,886 A | 12/1912 | Reay | |
| 1,230,561 A | 6/1917 | Chige | |
| 1,268,171 A | 6/1918 | Spaulding | |
| 1,493,515 A | 5/1924 | Berthold | |
| 1,758,261 A | 5/1930 | Leland | |

(Continued)

FOREIGN PATENT DOCUMENTS

CA 2211694 2/1998

(Continued)

OTHER PUBLICATIONS

User Manual *Tominator™ Stent Crimping Equipment* (Undated).

(Continued)

*Primary Examiner*—Monica A Huson
(74) *Attorney, Agent, or Firm*—Fulwider Patton LLP (57) ABSTRACT

A method of mounting a drug delivery stent on a balloon of a balloon catheter. The method securely mounts the drug delivery stent on the balloon without damaging the drug delivery layer of the stent. In one embodiment, the method generally comprises positioning a drug delivery stent on a balloon of a balloon catheter, and positioning the balloon with the drug delivery stent thereon within a polished bore of a mold formed at least in part of a metallic material. The balloon is pressurized and heated within the mold as the mold radially restrains the stent from expanding, to mount the stent on the balloon without damaging the drug delivery layer of the stent.

20 Claims, 5 Drawing Sheets

U.S. PATENT DOCUMENTS

| | | |
|---|---|---|
| 2,079,498 A | 5/1937 | Douglas |
| 2,452,857 A | 11/1948 | Mesaros |
| 2,465,433 A | 3/1949 | Doniger |
| 2,553,479 A | 5/1951 | Schmarje et al. |
| 2,964,088 A | 12/1960 | Erath |
| 3,164,042 A | 1/1965 | Hanna et al. |
| 3,203,078 A | 8/1965 | Ustin |
| 3,350,908 A | 11/1967 | Andrews et al. |
| 3,439,519 A | 4/1969 | Gerding |
| 3,496,684 A | 2/1970 | Banning et al. |
| 3,568,495 A | 3/1971 | Duffield et al. |
| 3,619,885 A | 11/1971 | Dischler |
| 3,898,987 A | 8/1975 | Jauhianen |
| 4,043,172 A | 8/1977 | Schmittou |
| 4,070,745 A | 1/1978 | Schimmelman |
| 4,107,964 A | 8/1978 | Smith |
| 4,215,871 A | 8/1980 | Hirsch et al. |
| 4,353,240 A | 10/1982 | Undin et al. |
| 4,373,923 A | 2/1983 | Kilwin |
| 4,379,397 A | 4/1983 | Langr |
| 4,454,657 A | 6/1984 | Yasumi |
| 4,455,854 A | 6/1984 | Ermolovich et al. |
| 4,468,224 A | 8/1984 | Enzmann et al. |
| 4,576,142 A | 3/1986 | Schiff |
| 4,606,347 A | 8/1986 | Fogarty et al. |
| 4,614,107 A | 9/1986 | Norin |
| 4,644,936 A | 2/1987 | Schiff |
| 4,681,092 A | 7/1987 | Cho et al. |
| 4,697,573 A | 10/1987 | Schiff |
| 4,703,546 A | 11/1987 | Gilbert |
| 4,786,271 A | 11/1988 | Menn |
| 4,838,264 A | 6/1989 | Bremer et al. |
| 4,864,924 A | 9/1989 | Storace |
| 4,901,707 A | 2/1990 | Schiff |
| 4,907,336 A | 3/1990 | Gianturco |
| 4,950,227 A | 8/1990 | Savin et al. |
| 4,961,291 A | 10/1990 | Lagasee |
| 4,987,722 A | 1/1991 | Koebbeman |
| 5,108,416 A | 4/1992 | Ryan et al. |
| 5,132,066 A | 7/1992 | Charlesworth et al. |
| 5,133,732 A | 7/1992 | Wiktor |
| 5,183,085 A | 2/1993 | Timmermans |
| 5,189,786 A | 3/1993 | Ishikawa et al. |
| 5,195,539 A | 3/1993 | Dyrud et al. |
| 5,207,960 A | 5/1993 | Moret de Rocheprise |
| 5,209,143 A | 5/1993 | Sweet |
| 5,209,799 A | 5/1993 | Vigil |
| 5,216,263 A | 6/1993 | Paoli |
| 5,217,434 A | 6/1993 | Arney |
| 5,263,969 A | 11/1993 | Phillips |
| 5,329,797 A | 7/1994 | Calhoun |
| 5,336,234 A | 8/1994 | Vigil et al. |
| 5,352,197 A | 10/1994 | Hammersmark et al. |
| 5,409,495 A | 4/1995 | Osborn |
| 5,437,083 A | 8/1995 | Williams et al. |
| 5,456,667 A | 10/1995 | Ham et al. |
| 5,465,716 A | 11/1995 | Avitall |
| 5,476,505 A | 12/1995 | Limon |
| 5,481,893 A | 1/1996 | Barjasteh et al. |
| 5,514,154 A | 5/1996 | Lau et al. |
| 5,540,124 A | 7/1996 | Srhoj |
| 5,546,646 A | 8/1996 | Williams et al. |
| 5,626,474 A | 5/1997 | Kukla et al. |
| 5,626,604 A | 5/1997 | Cottone, Jr. |
| 5,628,754 A | 5/1997 | Shevlin et al. |
| 5,630,830 A | 5/1997 | Verbeek |
| 5,632,760 A | 5/1997 | Sheiban et al. |
| 5,653,691 A | 8/1997 | Rupp et al. |
| 5,658,181 A | 8/1997 | Brown, II |
| 5,672,169 A | 9/1997 | Verbeek |
| 5,693,066 A | 12/1997 | Rupp et al. |
| 5,695,498 A | 12/1997 | Tower |
| 5,695,515 A | 12/1997 | Orejola |
| 5,715,723 A | 2/1998 | Owens |
| 5,725,519 A | 3/1998 | Penner et al. |
| 5,727,411 A | 3/1998 | Sakakibara et al. |
| 5,738,674 A | 4/1998 | Williams et al. |
| 5,746,764 A | 5/1998 | Green et al. |
| 5,759,474 A | 6/1998 | Rupp et al. |
| 5,782,855 A | 7/1998 | Lau et al. |
| 5,782,903 A | 7/1998 | Wiktor |
| 5,783,227 A | 7/1998 | Dunham |
| 5,785,715 A | 7/1998 | Schatz |
| 5,787,572 A | 8/1998 | Toms et al. |
| 5,795,289 A | 8/1998 | Wyttenbach |
| 5,807,520 A | 9/1998 | Wang et al. |
| 5,810,838 A | 9/1998 | Solar |
| 5,810,871 A | 9/1998 | Tuckey et al. |
| 5,810,873 A | 9/1998 | Morales |
| 5,836,952 A | 11/1998 | Davis et al. |
| 5,836,965 A | 11/1998 | Jenderse et al. |
| 5,860,966 A | 1/1999 | Tower |
| 5,893,852 A | 4/1999 | Morales |
| 5,893,867 A | 4/1999 | Bagaoisan et al. |
| 5,911,452 A | 6/1999 | Yan |
| 5,920,975 A | 7/1999 | Morales |
| 5,931,851 A | 8/1999 | Morales |
| 5,935,135 A | 8/1999 | Bramfitt et al. |
| 5,938,696 A | 8/1999 | Goicoechea et al. |
| 5,944,735 A | 8/1999 | Green et al. |
| 5,947,993 A | 9/1999 | Morales |
| 5,948,191 A | 9/1999 | Solovay |
| 5,951,569 A | 9/1999 | Tuckey et al. |
| 5,954,740 A | 9/1999 | Ravenscroft et al. |
| 5,968,069 A | 10/1999 | Dusbabek et al. |
| 5,972,016 A | 10/1999 | Morales |
| 5,974,652 A | 11/1999 | Kimes et al. |
| 5,976,181 A | 11/1999 | Whelan et al. |
| 6,009,614 A | 1/2000 | Morales |
| 6,024,737 A | 2/2000 | Morales |
| 6,027,510 A | 2/2000 | Alt |
| 6,051,002 A | 4/2000 | Morales |
| 6,063,092 A | 5/2000 | Shin |
| 6,063,102 A | 5/2000 | Morales |
| 6,082,990 A | 7/2000 | Jackson et al. |
| 6,092,273 A | 7/2000 | Villareal |
| 6,108,886 A | 8/2000 | Kimes et al. |
| 6,125,523 A | 10/2000 | Brown et al. |
| 6,141,855 A | 11/2000 | Morales |
| 6,159,229 A | 12/2000 | Jendersee et al. |
| 6,167,605 B1 | 1/2001 | Morales |
| 6,176,116 B1 | 1/2001 | Wilhelm et al. |
| 6,202,272 B1 | 3/2001 | Jackson |
| 6,289,568 B1 | 9/2001 | Miller et al. |
| 6,293,959 B1 | 9/2001 | Miller et al. |
| 6,360,577 B2 | 3/2002 | Austin |
| 6,395,008 B1 | 5/2002 | Ellis et al. |
| 6,468,299 B2 | 10/2002 | Stack et al. |
| 6,510,722 B1 | 1/2003 | Ching et al. |
| 6,571,719 B2 | 6/2003 | MacDonald |
| 6,585,747 B1 | 7/2003 | Limon et al. |
| 6,620,193 B1 | 9/2003 | Lau et al. |
| 6,629,991 B1 | 10/2003 | Lau et al. |
| 6,666,880 B1 | 12/2003 | Chiu et al. |
| 6,689,123 B2 | 2/2004 | Pinchasik et al. |
| 6,835,059 B2 | 12/2004 | Skinner et al. |
| 2001/0001890 A1 | 5/2001 | Austin |
| 2003/0204238 A1 | 10/2003 | Tedeschi |
| 2003/0208254 A1 | 11/2003 | Shortt |
| 2004/0177805 A1 | 9/2004 | Hijlkema et al. |

2006/0100694 A1    5/2006    Globerman

FOREIGN PATENT DOCUMENTS

| | | |
|---|---|---|
| DE | 464004 | 7/1928 |
| DE | 297 14857 U1 | 11/1997 |
| DE | 198 13 854 | 9/1999 |
| EP | 0 303 889 B1 | 6/1993 |
| EP | 0553960 A1 | 8/1993 |
| EP | 0 562 478 B1 | 12/1994 |
| EP | 0 630 623 A2 | 12/1994 |
| EP | 0 697 226 A1 | 2/1996 |
| EP | 0 826 346 A1 | 3/1998 |
| EP | 0 873 731 A1 | 10/1998 |
| EP | 0 916 318 A1 | 5/1999 |
| EP | 0 938 877 AW | 9/1999 |
| EP | 0 938 880 A3 | 11/1999 |
| EP | 1295570 | 3/2003 |
| FR | 975797 | 3/1951 |
| GB | 159065 | 2/1921 |
| GB | 2 088 811 A | 6/1982 |
| JP | 02180275 | 7/1990 |
| JP | 747135 | 2/1995 |
| JP | 767967 | 3/1995 |
| JP | 1119230 | 1/1999 |
| WO | WO 93/06780 | 4/1993 |
| WO | WO 97/09946 | 3/1997 |
| WO | WO 98/14120 | 4/1998 |
| WO | WO 98/19633 | 5/1998 |
| WO | WO 99/43473 | 9/1999 |
| WO | WO 99/55406 | 11/1999 |
| WO | WO 01/21103 | 3/2001 |
| WO | 2005053937 | 6/2005 |
| WO | 2006110861 | 10/2006 |

OTHER PUBLICATIONS

Bard XT Stent Brochure: *The cXTraordinary Sent* (Undated).

*Corporate Profile—Machine Solutions, Inc.*, Reprinted from *European Medical Device Manufacturer*, Jul./Aug. 2000, Copyright© 2000 Canon Communications LLC.

MSI Equipment pages, www.machinesolutions.org Copyright© 2002 Machine Solutions, Inc.

METHOD OF STENT MOUNTING TO FORM A BALLOON CATHETER HAVING IMPROVED RETENTION OF A DRUG DELIVERY STENT

BACKGROUND OF THE INVENTION

This invention relates generally to catheters, and particularly intravascular stent delivery catheters.

In percutaneous transluminal coronary angioplasty (PTCA) procedures a guiding catheter is advanced in the patient's vasculature until the distal tip of the guiding catheter is seated in the ostium of a desired coronary artery. A guidewire is first advanced out of the distal end of the guiding catheter into the patient's coronary artery until the distal end of the guidewire crosses a lesion to be dilated. A dilatation catheter, having an inflatable balloon on the distal portion thereof, is advanced into the patient's coronary anatomy over the previously introduced guidewire until the balloon of the dilatation catheter is properly positioned across the lesion. Once properly positioned, the dilatation balloon is inflated with inflation fluid one or more times to a predetermined size at relatively high pressures so that the stenosis is compressed against the arterial wall and the wall expanded to open up the vascular passageway. Generally, the inflated diameter of the balloon is approximately the same diameter as the native diameter of the body lumen being dilated so as to complete the dilatation but not overexpand the artery wall. After the balloon is finally deflated, blood flow resumes through the dilated artery and the dilatation catheter and the guidewire can be removed therefrom.

In such angioplasty procedures, there may be restenosis of the artery, i.e. reformation of the arterial blockage, which necessitates either another angioplasty procedure, or some other method of repairing or strengthening the dilated area. To reduce the restenosis rate of angioplasty alone and to strengthen the dilated area, physicians now normally implant an intravascular prosthesis, generally called a stent, inside the artery at the site of the lesion. Stents may also be used to repair vessels having an intimal flap or dissection or to generally strengthen a weakened section of a vessel or to maintain its patency. Stents are usually delivered to a desired location within a coronary artery in a contracted condition on a balloon of a catheter which is similar in many respects to a balloon angioplasty catheter, and expanded within the patient's artery to a larger diameter by expansion of the balloon. The balloon is deflated to remove the catheter and the stent left in place within the artery at the site of the dilated lesion. See for example, U.S. Pat. No. 5,507,768 (Lau et al.) and U.S. Pat. No. 5,458,615 (Klemm et al.), which are incorporated herein by reference.

The stent must be securely yet releasably mounted on the catheter balloon for delivery and deployment at the desired location in a patient's body lumen. If the stent becomes dislodged from or moved relative to the balloon during delivery, the system will not correctly implant the stent in the body lumen. However, the stent can't be so strongly fixed to the balloon that it inhibits expansion of the balloon and/or release of the stent once the balloon is positioned at the desired location. One difficulty has been retention of a stent having a drug delivery layer. The mounting process used to secure the drug delivery stent to the balloon must not damage the drug or the matrix material containing the drug. It would be a significant advance to provide a catheter balloon having improved retention of a drug delivery stent, and without inhibiting balloon or stent function. The present invention satisfies these and other needs

SUMMARY OF THE INVENTION

The invention is directed to a method of mounting a drug delivery stent on a balloon, and a stent delivery balloon catheter produced therefrom. The method securely mounts the drug delivery stent on the balloon without damaging the drug delivery layer of the stent.

In one embodiment, the method generally comprises positioning a drug delivery stent on a balloon of a balloon catheter, the stent having a drug delivery layer, and positioning the balloon with the drug delivery stent thereon within a polished bore of a mold formed at least in part of a metallic material. The balloon is pressurized and heated within the mold to mount the stent on the balloon, without damaging the drug delivery layer of the stent. The mold radially restrains the stent from expanding when the balloon is pressurized therein, so that the balloon can be forced into the gaps in the stent wall using inflation pressures higher than those which normally cause radial expansion of the stent. The bore of the mold is defined by a polished inner surface with a polished finish which is sufficiently smooth so that contact and relative movement between the stent and polished inner surface of the mold does not roughen or otherwise damage or create a texture on the drug delivery layer of the stent. As a result, the release rate of the drug from the drug delivery layer is substantially equal to the release rate prior to stent mounting. In one embodiment, the smooth surface of the drug delivery layer, which is free of roughness and irregularities caused by the stent mounting, provides the drug delivery layer with a uniform thickness which is within the normal variance produced by the method used to form the drug delivery layer. Additionally, the inner surface of the mold does not cause the drug delivery layer to transfer drug to the inner surface of the mold during the stent mounting, so that the amount of drug present in the drug delivery layer is substantially equal to the amount prior to stent mounting.

In a presently preferred embodiment, the drug delivery layer of the stent is a coating applied to a surface of the radially expandable tubular body of the stent. However, a variety of suitable configurations may be used as are well known in the art, including embodiments in which the tubular body of the stent is itself formed of a drug delivery matrix, or the drug delivery layer is a tubular sleeve on a surface of the body of the stent. Additionally, the drug delivery layer should be understood to broadly refer to configurations which deliver or present one or more drugs by any of a variety of suitable mechanisms including eluting the drug from the layer, bioabsorption of a drug delivery matrix, and the like. The stent may be biostable and/or bioabsorable. The terminology "drug" as used herein should be understood to refer to a variety of therapeutic and diagnostic agents. In a presently preferred embodiment, the drug is intended to prevent or inhibit restenosis.

The balloon is heated by heating the mold using a heat transfer medium which provides temperature control to the mold with a tolerance of about ±1 degree to about ±2 degrees Fahrenheit (F)). In one embodiment, heating the mold comprises submerging the mold in a liquid bath, or contacting the surface of the mold with a conductive heating element. As a result, the heat transfer medium heats the mold primarily by conduction, and provides for finer temperature control and quicker heating than is provided by heating methods which heat primarily by convection (e.g., heating with hot air). In contrast, heating with hot air provides a heating tolerance of about ±10 degrees. In a presently preferred embodiment, the heat transfer medium is a conductive heating element such as a platen (e.g., a heated flat metal plate) configured to provide uniform heating of the balloon within the mold when the platen is in contact with the mold. Thus, the temperature is uniform (i.e., within about ±2 degrees F.) along the length of the section of the mold exposed to the heating medium, and the temperature at any given point of the heated length remains constant (i.e., within ±2 degrees F.) during the heating. With the metal platen pressed against an outer surface of the mold, the platen heats purely by conduction (unlike a hot circulating heating medium which heats by both conduction and convention), and provides for finer temperature control at the surface of the mold than a hot liquid bath or hot air. The temperature control provided by the heat transfer medium prevents the drug from being exposed to an elevated temperature which is above the thermal limit of the drug, while allowing the balloon to be quickly heated to a sufficiently high temperature to soften the balloon material during stent mounting.

In the embodiment in which the heat transfer medium is a hot liquid bath, the mold is configured to seal the bore of the mold with the catheter therein, so that the mold is submerged without liquid or humidity from the liquid bath contacting the drug delivery stent in the mold. As a result, the drug delivery layer is not dissolved or otherwise damaged by exposure when the mold is submerged in the liquid bath.

The metallic material of the mold allows the mold to be machined with tight dimensional tolerances, to provide an accurate and uniform bore diameter. Additionally, the metallic material of the mold provides sufficient strength, even at elevated temperature, so that the mold radially restrains the stent during the stent mounting procedure without the diameter of the mold bore increasing. Thus, unlike a radial restraining member which expands somewhat during pressurization of the balloon therein, the mold of the invention controls the outer diameter of the mounted stent, so that the profile of the mounted stent is not disadvantageously increased during the stent mounting. The profile of the mounted stent can impact the ability of the stent delivery balloon catheter to advance and cross tight lesions in the patient's vasculature.

The mold is a split-mold having hinged halves. The mold halves swing open and close at the hinge so that the balloon with the stent thereon can be introduced or removed from the mold without damaging the drug delivery layer of the stent. The mold therefore prevents or inhibits the damage to the drug delivery layer which can otherwise occur with tubular radial restraining members which don't open up for introduction of the balloon catheter and which must be cut off the balloon catheter after the stent mounting. Additionally, the mold of the invention is reusable, and provides for accurate, uniform heating which does not vary with each subsequent use.

In a presently preferred embodiment, the mold body defining the entire length of the bore and outer surface of the mold is formed of metal. As a result, the metal mold substantially uniformly heats the entire length of the balloon within the bore of the mold. However, in alternative embodiments, the mold has a body with a heat conducting metallic section and an insulating non-metal section, so that heating the mold selectively heats sections of the balloon within the bore of the mold. The insulating section of the mold insulates the drug-delivery stent during the stent mounting procedure, so that the drug delivery stent is heated to a lower temperature than the inflatable sections of the balloon at either end of the stent. As a result, the balloon is sufficiently heated for the stent mounting procedure without exposing the drug-delivery stent to a disadvantageously high temperature (e.g., a temperature above the thermal limit of the drug).

A stent delivery balloon catheter of the invention generally comprises an elongated shaft having an inflation lumen and a guidewire lumen, a balloon on a distal shaft section having an interior in fluid communication with the inflation lumen, and a stent releasably mounted on the balloon for delivery and deployment within a patient's body lumen. The stent typically comprises an open-walled body of stent struts with gaps between adjacent struts. The balloon typically has a folded noninflated configuration with wings wrapped around the circumference of the balloon. In alternative embodiments, the balloon is a wingless balloon which expands by stretching from a wingless noninflated configuration.

One embodiment of the invention is directed to a mold having a stepped inner diameter comprising enlarged inner diameter sections on either end of a middle section. During stent mounting, the stepped inner diameter forms one or more external shoulders in the balloon. The balloon shoulders are located adjacent the end(s) of the stent, to prevent or inhibit the stent from moving longitudinally relative the balloon during delivery and deployment of the stent. The balloon external shoulders have an outer diameter larger than the outer diameter of the unexpanded stent, and thus provide a barrier that the stent would have to overcome in order to move longitudinally relative to the balloon. The external shoulders are thus molded into the balloon material during stent mounting and are not the result of material added to the shaft or balloon. As a result, the shoulders are formed without affecting the stiffness transitions of the catheter.

Another aspect of the invention is directed to a method of mounting a stent on a stent delivery balloon catheter using the mold having a stepped inner diameter. The method generally comprises introducing inflation media into the interior of the balloon, and heating the balloon, to radially expand the balloon with the stent restrained from radially expanding by a mold around an outer surface of the stent, so that the balloon expands into the stent gaps to embed the stent in an outer surface of the balloon, to thereby mount the stent on the balloon, wherein the mold has a stepped inner diameter so that expanding the balloon forms at least one shoulder in the balloon adjacent an end of the stent with an outer diameter greater than an outer diameter of the mounted stent in an unexpanded configuration.

The invention provides a method of mounting a drug delivery stent on a catheter balloon which provides a low profile mounted stent, and which securely and consistently mounts the stent on the balloon for delivery and deployment within a patient's body lumen without damaging the drug delivery layer of the stent. The metallic mold, heated primarily by conduction during stent mounting, allows temperature control to the mold sufficient to prevent heat damage of the drug delivery layer. The mold is heated with a method configured to avoid the nonuniformity and irreproducibility of convective heat transfer. Additionally, the mold is configured to prevent or reduce roughening or otherwise mechanically damaging the drug delivery layer, so that the drug delivery layer release rate and drug amount are not disadvantageously effected by the stent mounting procedure of the invention. In an embodiment of the invention in which the mold has heat conducting portions and insulating portions, heating the mold selectively heats sections of the balloon and stent within the bore of the mold. In another embodiment of the invention directed to a mold with a stepped inner diameter, the mold produces one or more shoulders in the balloon which enhance stent retention on the balloon. These and other advantages of the invention will become more apparent from the following detailed description and exemplary drawings.

DETAILED DESCRIPTION OF THE PREFERRED EMBODIMENTS

Figure 1:
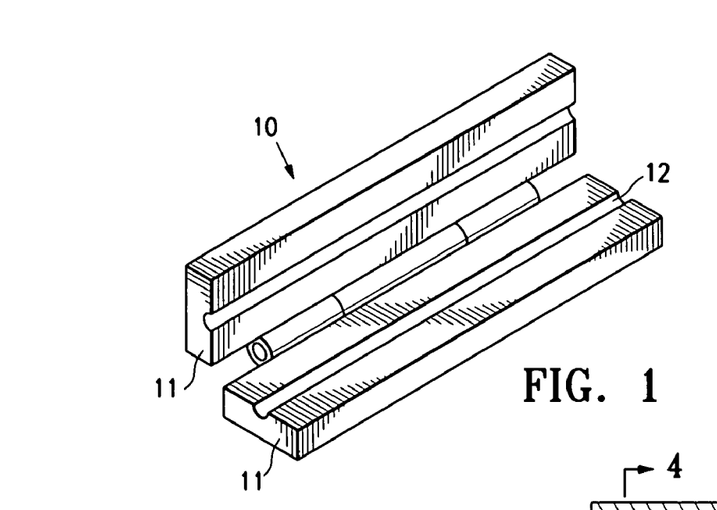
FIG. 1 is an isometric view of a mold useful in a method which embodies features of the invention, in which a drug delivery stent is mounted onto a balloon catheter.
Figure 2:
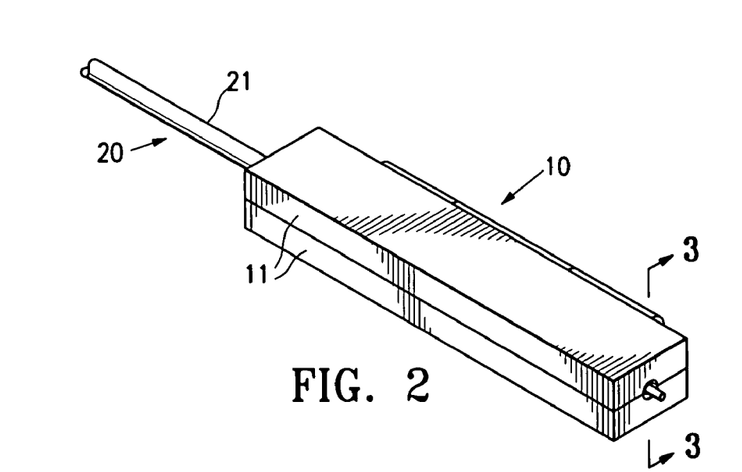
FIG. 2 is an isometric view of the mold of FIG. 1 in a closed configuration, illustrating a distal section of a balloon catheter within the mold.

FIG. 1 illustrates a metal mold 10 useful in a method of mounting a drug delivery stent on a balloon catheter, embodying features of the invention. Mold 10 generally comprises a split metal body 11 with a bottom half, a top half, and a polished bore 12 configured to receive a balloon catheter therein. In the embodiment illustrated in FIG. 1, the top and bottom halves of the mold are joined by a hinge, and the mold is illustrated in an open configuration. FIG. 2 illustrates the mold in a closed configuration with a distal section of a balloon catheter 20 in position within the mold.

Figure 3:
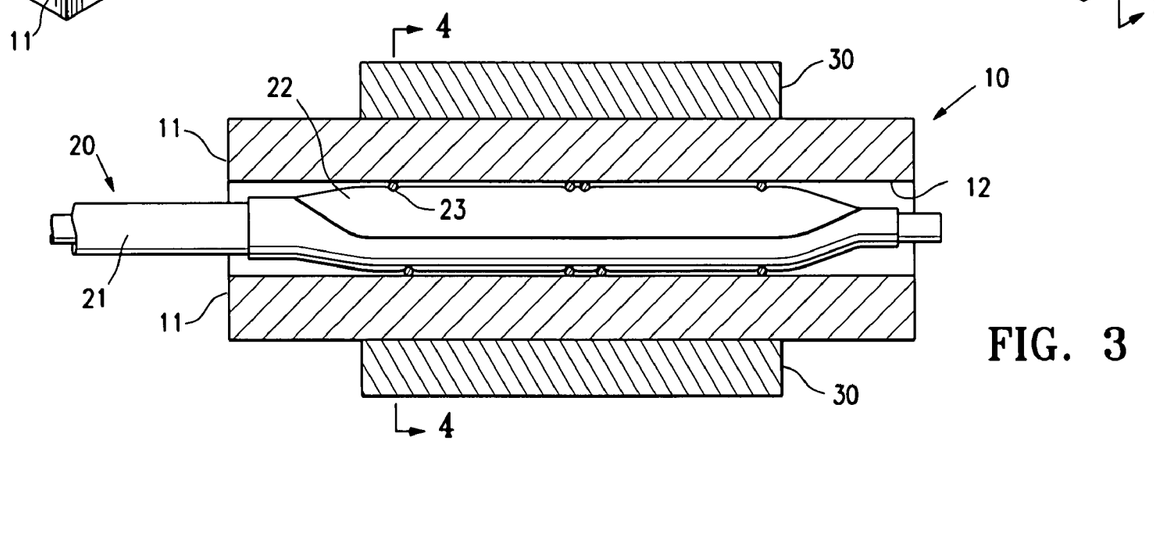
FIG. 3 is a longitudinal cross sectional view illustrating the mold of FIG. 2 with heating platens on an outer surface of the mold during a method of mounting a drug delivery stent on the balloon of the balloon catheter.
Figure 4:
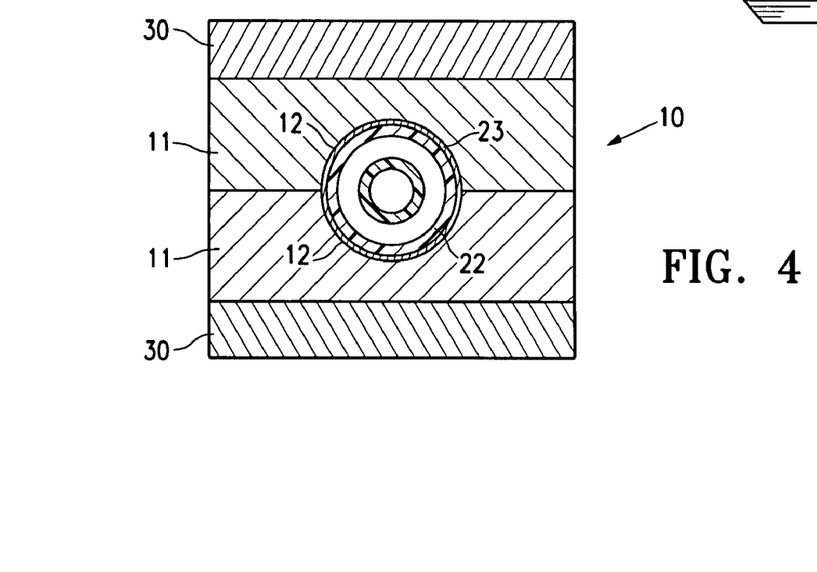
FIG. 4 is a diagrammatic transverse cross section of the assembly of FIG. 3, taken along line 4-4.

FIG. 3 illustrates the mold 10 with the distal section of the balloon catheter 20 therein, partially in longitudinal cross section, during a method of mounting a drug delivery stent on the balloon catheter 20. The balloon catheter 20 has an elongated shaft 21 with a balloon 22 on a distal section thereof and a drug delivery stent 23 on the balloon. The balloon 22, with the drug delivery stent 23 thereon, are completely contained within the polished bore 12 of the mold 10. FIG. 4 illustrates a diagrammatic transverse cross sectional view of FIG. 3, taken along line 4-4.

Figure 5:
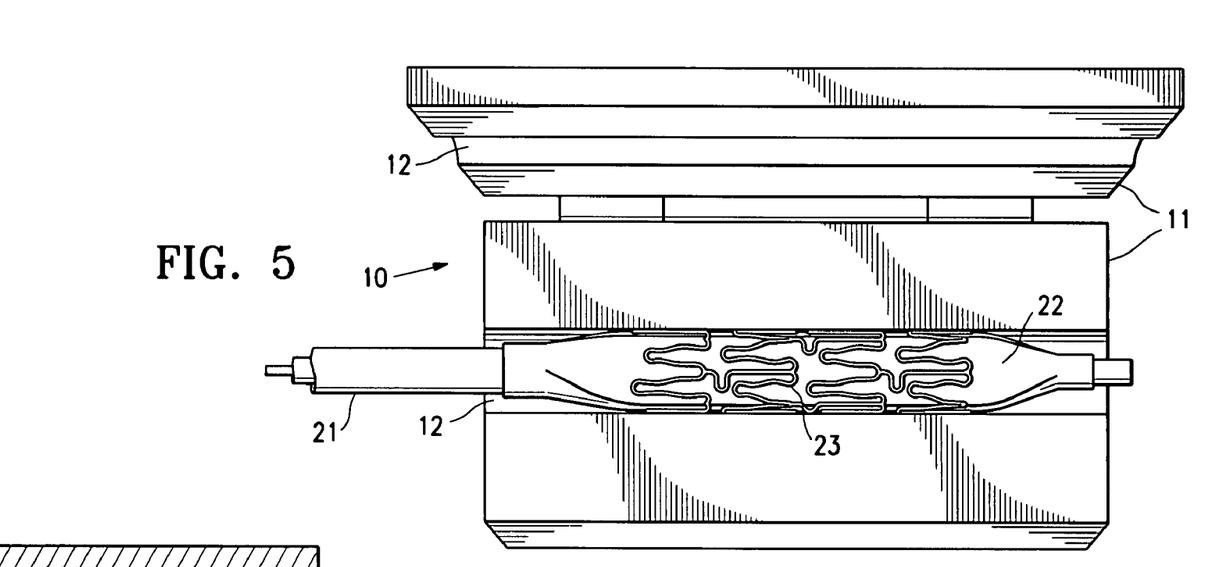
FIG. 5 is a perspective view of the mold of FIG. 3 in an open configuration allowing for removal from the mold of the stent delivery balloon catheter having the drug delivery stent mounted on the balloon.

A method of releasably mounting the drug delivery stent 23 on the balloon 22 generally comprises positioning the drug delivery stent 23 on the uninflated balloon 22 of the balloon catheter 20. The stent is typically mechanically crimped (i.e., radially collapsed) down onto the balloon 22. A distal end section of the catheter 20 is placed within the mold, to position the balloon with the crimped stent 23 thereon within the polished bore 12 of the mold 10. The hinged halves of the mold are closed together, and the balloon 22 is pressurized by introducing inflation fluid into the interior of the balloon 22 and heated to an elevated temperature. In a presently preferred embodiment, the balloon is pressurized and then heated in the pressurized condition. In an alternative embodiment, the balloon is simultaneously pressurized and heated. The balloon material at the elevated temperature and pressure is forced into the gaps in the wall of the stent 23, to embed the stent within the outer surface of the balloon. FIG. 3 illustrates the balloon in the pressurized and heated state, with the stent contacting the polished inner surface of the bore of the mold to radially restrain the stent from radially expanding. In one embodiment, the balloon is pressurized to a relatively high pressure of about 15 to about 23 atm, more specifically about 19 to about 21 atm. The balloon is then cooled in the mold prior to depressurization of the balloon, and the cooled balloon depressurized, and the balloon catheter removed from the mold with the stent mounted on the balloon. FIG. 5 illustrates the mold 10 in an open configuration facilitating removal of the balloon catheter 20 therefrom after the stent 23 is mounted onto the balloon 22.

The mold bore 12 is defined by a polished inner surface of the top and bottom halves of the mold. In a presently preferred embodiment, the polished inner surface has a polish finish of about 0.4 microns or less. The bore is polished by techniques known in the art, such as honing. The polished inner surface contacts the stent, and provides a smooth surface which prevents or inhibits roughening the surface of the drug delivery stent 23 during the stent mounting procedure.

In the embodiment illustrated in FIGS. 1-5, the diameter of the bore 12 is the same along the entire length of the mold 10. The bore 12 is preferably formed by machining so that the diameter of the bore is highly accurate and uniform (i.e., the diameter varies by no more than ±0.025 mm along the length of the mold, and multiple molds can be made having the same dimensions). The bore 12 is preferably machined within the block which forms the body of the mold 10, with the two halves of the mold 10 in place together during the machining. As a result, the top and bottom sections of the bore 12 perfectly and repeatably mate together when the two halves of the mold 10 are closed together. In a presently preferred embodiment, the diameter of the mold bore 12 is slightly larger than the outer diameter of the crimped stent 23 on the balloon 22. As a result, the diameter of the mold bore 12 is large enough to avoid scuffing/damaging the drug delivery layer of the stent 23 when the balloon 22 and stent 23 crimped thereon are placed within the bore 12, while being sufficiently small so that expansion of the crimped stent 23 during the stent mounting is minimized. In an alternative embodiment, the diameter of the mold bore 12 is equal to the diameter of the crimped stent 23 on the balloon 22, so that the stent does not radially expand during the stent mounting. Each half of the mold 10 preferably has relatively thin walls, e.g., with a wall thickness of not greater than about 0.25 to about 0.5 mm, at its thinnest along a midline of the bore 12 of the mold (i.e., the wall thickness from the outer surface of the mold half to the bore), to provide fast heating and cooling within the bore 12 of the mold 10.

In accordance with the invention, the balloon 22 is heated by heating the mold 10 with a heat transfer medium which provides very accurate temperature control to the mold 10. In the embodiment illustrated in FIG. 3, the heat transfer medium is a conductive heating element member in the form of metal platens 30. The metal platens 30 have a heating element (not shown) such as a resistive heater which heats the metal of the platens, and an inner surface typically configured to correspond to the outer surface of the mold 10. In the illustrated embodiment, the inner surface of the platens 30 and the outer surface of the mold 10 are flat, although, in alternative embodiments (not shown), the surfaces have irregular mating surfaces designed to increase the surface area thereof. The temperature at the surface of the platens 30 is very accurately controllable, so that, with the surface of the metal platens 30 pressed against the outer surface of the mold 10, the temperature of the mold can be very accurately controlled (i.e., with a tolerance which is not larger than about ±2 degrees F., more preferably with a tolerance of about ±1 degree F.).

With the balloon catheter 20 in position within the bore 12 of the mold 10, the mold 10 is slid into the space between the metal platens 30, and the metal platens 30 brought into contact with the outer surface of the top and bottom halves of the mold, to thereby heat the mold 10. The mold 10 is heated to an elevated temperature sufficient to soften the balloon 22 but lower than the thermal limit of the drug of the drug delivery stent 23. In a presently preferred embodiment, the temperature within the mold 10 is below a temperature which would cause the drug delivery layer of the stent 23 to flow. However, in an alternative embodiment in which the drug delivery layer of stent 23 is heated and flows somewhat at the elevated temperature, the smooth inner surface of the polished bore 12 causes the drug delivery layer to remain uniform in thickness without a roughened or irregular exterior. In one embodiment, the mold 10 is heated to a temperature of about 160° F. to about 190° F., with the balloon catheter 20 therein during the stent mounting procedure, to soften a balloon formed of polymeric material.

The metal platens 30 have a relatively high thermal conductivity, higher than that of air at least in the temperature range of interest, providing a relatively fast rate of heating. In one embodiment, the mold 10 is in contact with the heating platens 30 for not greater than about 120 seconds, and more specifically for about 60 to about 120 seconds during the stent mounting procedure. In contrast, hot air would take significantly longer, and for example not less than about 120 seconds (e.g., on the order of about 120 to about 240 seconds), to heat the mold to the desired temperature. The platens 30 and mold 10 are configured to provide a fast heating rate in combination with fine control of the elevated temperature, for improved mounting of the drug delivery stent 23 without damage to the drug delivery layer.

The platens 30 have a length which, in one embodiment, is at least as long as the stent 23, and the platens are brought into contact with a length of the mold 10 corresponding to the location of the drug delivery stent 23 therein. In the embodiment illustrated in FIG. 3, the platens are longer than the stent but shorter than the balloon, although a variety of suitable configurations can be used including platens having a length which is shorter than the stent, or platens having a length equal to the length of the mold 10. In a presently preferred embodiment, the platens have a length which is at least as long as, or substantially equal to, the length of the inflatable section of the balloon (i.e., the working length and tapered sections). Although discussed primarily in terms of the embodiment in which the mold is heated with platens 30, alternative heating mediums that heat primarily by conduction can be used including a hot liquid bath. In the embodiment using a hot liquid bath (not shown), the mold 10 has seals (not shown) at either end of the mold which seal around the balloon catheter 20 to prevent the liquid or humidity of the hot liquid bath from contacting the drug delivery stent 23 within the mold 10 when the mold is submerged within the bath.

Figure 6:
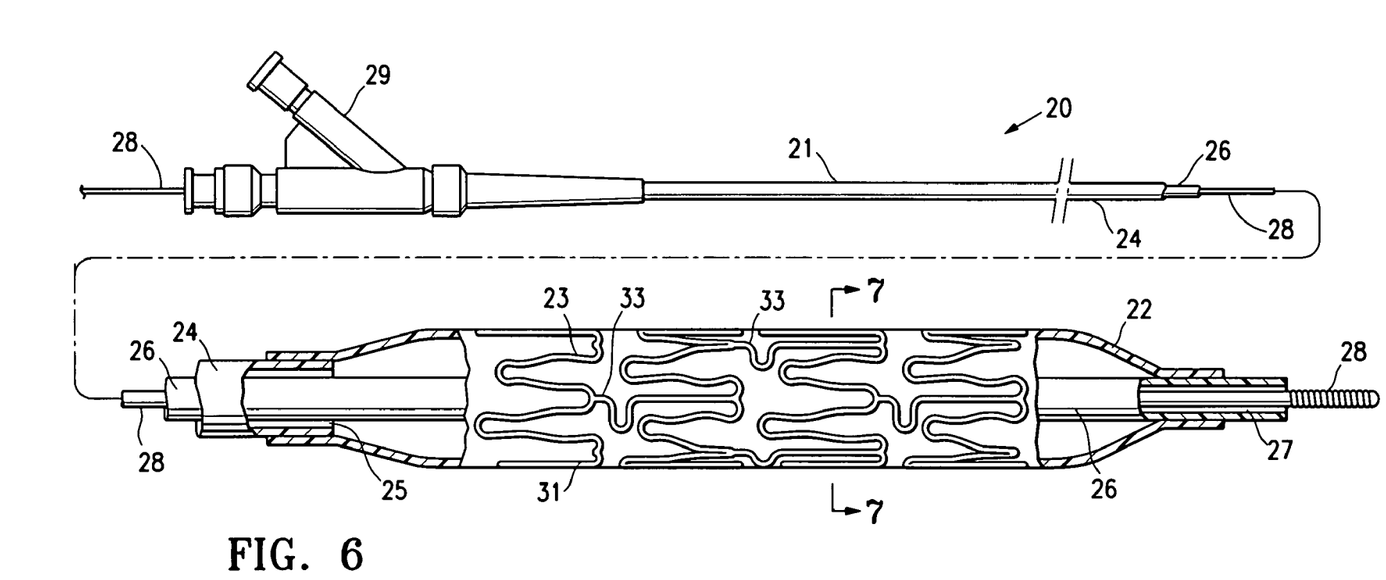
FIG. 6 is an elevational view of the stent delivery balloon catheter of FIG. 5 after being removed from the mold.
Figure 7:
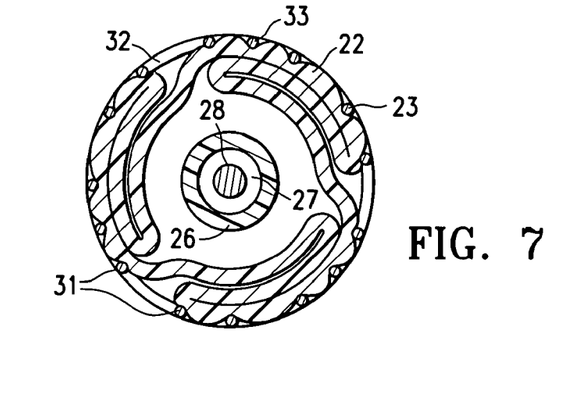
FIG. 7 is a transverse cross sectional view of the stent delivery balloon catheter of FIG. 6, taken along line 7-7.

FIG. 6 illustrates the stent delivery balloon catheter 20 embodying features of the invention, after removal from the mold 10 with the drug delivery stent 23 mounted on the balloon 22. In the illustrated embodiment, the catheter shaft 21 comprises an outer tubular member 24 defining an inflation lumen 25 therein, and an inner tubular member 26 defining a guidewire lumen 27 therein configured to slidingly receive a guidewire 28. Specifically, in the illustrated embodiment, the coaxial relationship between outer tubular member 24 and inner tubular member 26 defines annular inflation lumen 25. In the embodiment illustrated in FIG. 6, the guidewire lumen 27 extends to the proximal end of the catheter. Inflatable balloon 22 has a proximal skirt section sealingly secured to the distal end of outer tubular member 24 and a distal skirt section sealingly secured to the distal end of inner tubular member 26, so that the balloon interior is in fluid communication with inflation lumen 25. An adapter 29 at the proximal end of catheter shaft 21 is configured to provide access to guidewire lumen 27, and to direct inflation fluid through the arm into inflation lumen 25. As best shown in FIG. 7 illustrating a transverse cross section of the balloon catheter of FIG. 6, taken along line 7-7, the stent gaps are partially filled by the balloon material so that the balloon material contacts and partially encapsulates the side surfaces of the stent struts, to securely mount the stent on the balloon. In an alternative embodiment (not shown), the balloon material completely fills the stent gaps to fully encapsulate the side surfaces of the stent struts. In the embodiment illustrated in FIGS. 6 and 7 the portions of the balloon which protrude between the stent struts have an outer surface flush with the outer surface of the stent.

FIG. 6 illustrates the balloon 22, in a folded configuration with wings wrapped around the circumference of the balloon prior to complete inflation of the balloon. The balloon 22 typically has two or more, and most preferably three wings in the noninflated configuration, which unwrap during inflation of the balloon 22. For ease of illustration, a substantial gap is illustrated between the inner surface of the inflatable balloon interior and the shaft inner tubular member 26 in FIGS. 6 and 7, although it should be understood that the noninflated balloon is typically collapsed down around to inner tubular member in the noninflated configuration. The balloon expands to a generally cylindrical inflated configuration with a central working length inflated section, a proximal inflated conical tapered section proximal to the stent (and distal to the proximal skirt section), and a distal inflated conical tapered section distal to the stent (and proximal to the distal skirt section). FIG. 6 illustrates the stent 23 mounted on the central, working length section of the balloon 22, prior to complete expansion. The distal end of catheter 20 may be advanced to a desired region of the patient's body lumen in a conventional manner with the balloon in the noninflated configuration, and the balloon 22 inflated by directing inflation fluid into the balloon interior to expand the stent 23. The balloon is then deflated, leaving the drug delivery stent 23 implanted in the body lumen.

The stent 23 generally comprises an open-walled tubular body of interconnected, spaced-apart stent struts 31 with gaps 32 between adjacent stent struts. In the illustrated embodiment, the stent struts 31 form rings which have a serpentine wave pattern of opposed turns and which are longitudinally spaced apart and connected by links 33. However, the stent 23 can have a variety of suitable configurations as are conventionally known. The tubular body of the stent 23 is typically a biostable material such as a metal, although it can alternatively be formed of a bioabsorable material. In a presently preferred embodiment, the drug delivery layer is a coating (not shown) applied to the surface of the tubular body of the stent 23.

Although the embodiment illustrated in FIG. 6 is directed to embedding the drug delivery stent 23 in the outer surface of the layer of a single-layered balloon, it should be understood that the balloon can alternatively be formed of multiple layers or with an outer sleeve member, so that embedding the stent into the balloon embeds the stent in the outer surface of the outer most layer or outer sleeve of the balloon.

Figure 8:
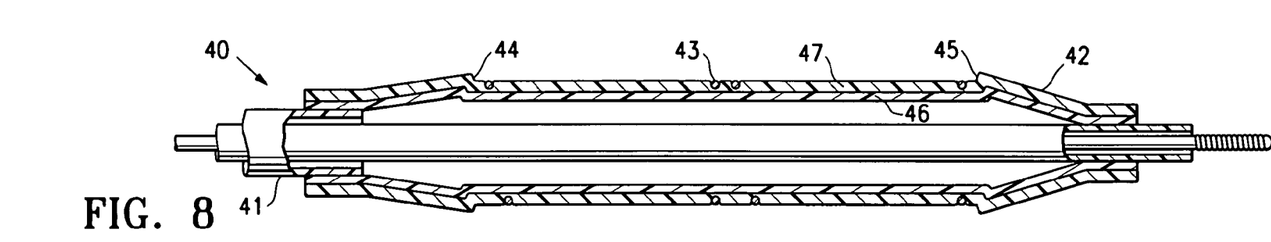
FIG. 8 illustrates a stent delivery balloon catheter embodying features of the invention, in which the balloon forms shoulders adjacent the ends of the stent.

FIG. 8 illustrates an alternative embodiment of a stent delivery balloon catheter 40 embodying features of the invention, having an elongated shaft 41 and a balloon 42 on a distal shaft section with a proximal external shoulder 44 adjacent a proximal end of the stent 43 with an outer diameter larger than the outer diameter of the nonexpanded stent mounted on the balloon, and a distal external shoulder 45 adjacent a distal end of the stent 43 with an outer diameter larger than the outer diameter of the nonexpanded stent mounted on the balloon. Alternatively, the balloon can have only one of the proximal 44 or distal 45 external shoulders. For example, in one embodiment (not shown), the balloon has the distal external shoulder 45, and not the proximal external shoulder 44. The external shoulders 44, 45 are located along the proximal and distal inflatable sections of the balloon (e.g., along the sections of the balloon which inflate to form the proximal and distal conical tapered sections in the inflated configuration, at the junction between the inflatable conical tapered section of the balloon and the end of the working length section). The stent 43 is similar to drug delivery stent 23 discussed above in relation to the embodiment of FIG. 1.

In the illustrated embodiment, the balloon 42 comprises an inner layer 46 and an outer sleeve member 47 which defines the outer surface of the external shoulders 44, 45. The outer sleeve 47 is typically formed of a relatively low melting point elastomeric polymer. In the embodiment illustrated in FIG. 8, molding the external shoulders 44, 45 in the outer sleeve 47 of the balloon also forms shoulders in the balloon inner layer 46.

The balloon 42 is illustrated in a partially inflated configuration in FIG. 8 for ease of illustration, but it should be understood that the working length of the balloon is typically collapsed down to the shaft inner tubular member in the noninflated configuration for advancement within the patient's body lumen. In one embodiment, the balloon inflates to a cylindrical, fully inflated configuration (i.e., with no shoulders 44, 45 in the outer surface of the expanded balloon). The shoulders 44, 45 thus substantially disappear as the balloon expands, with the working length of the balloon expanding to define the maximum inflated diameter of the balloon, and the conical sections on either end of the working length section tapering away from the working length section to a smaller outer diameter in the inflated configuration.

Figure 9:
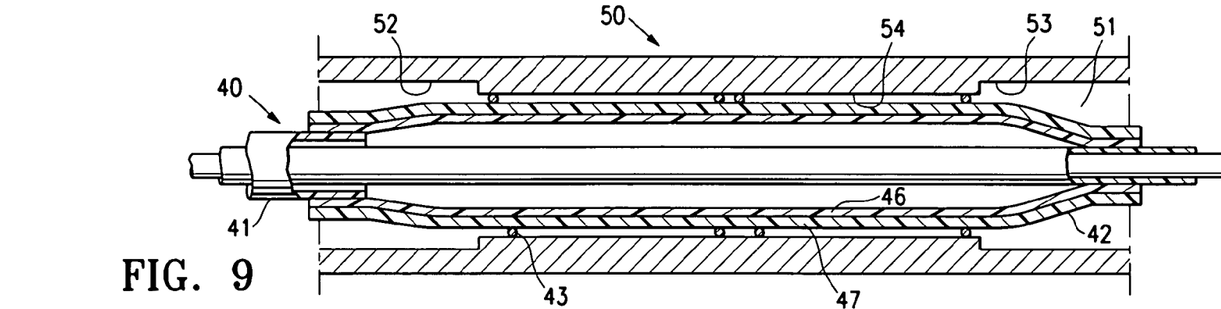
FIG. 9 illustrates a mold useful in a method of mounting a stent on a balloon catheter, having a stepped inner diameter, to form the shoulders in the balloon.

In a method of mounting the stent 43 on the balloon catheter 40 to form the stent delivery system of FIG. 8, the radial restraining mold 50 has a stepped inner diameter which forms the external shoulders 44, 45 in the balloon during the stent gripping. FIG. 9 illustrates balloon catheter 40 within a radial restraining mold 50 having an inner chamber 51 configured for receiving the balloon portion of the balloon catheter 40. The radial restraining mold 50, similar to the embodiment of FIG. 1, typically has a bottom half attached by hinges to a top half, which facilitates positioning the balloon portion of the catheter in the inner chamber 51 of the mold. The inner chamber 51 has enlarged inner diameter sections 52 and 53 on either end of a middle section 54. The balloon is illustrated with the outer sleeve 47 and stent 43 thereon, during pressurization of the balloon to mount the stent on the balloon. As set forth above, the mold 50 radially restrains the stent 43 as inflation media is introduced into the interior of the balloon and the mold is heated to heat the balloon, so that the balloon expands into the stent gaps and the external shoulders 44, 45 are formed in the balloon by the enlarged inner diameter sections 52, 53 of the mold 50. In the embodiment illustrated in FIG. 8, the inner surface of the balloon also has a stepped configuration at the shoulders. As a result, a gap exists between the inner surface of the balloon at the shoulders 44, 45 and the outer surface of the shaft (or the outer surface of a radiopaque marker (not shown) on the shaft if the radiopaque marker is located beyond the end of the stent) in the noninflated configuration. Although the embodiment illustrated in FIGS. 8 and 9 has the outer sleeve 47 on the balloon inner layer 46, it should be understood that in an alternative embodiment (not shown) the outer sleeve 47 is omitted. The method fully or partially embeds the stent 43 in the balloon 42 depending on the balloon material and stent mounting method conditions.

Figure 10:
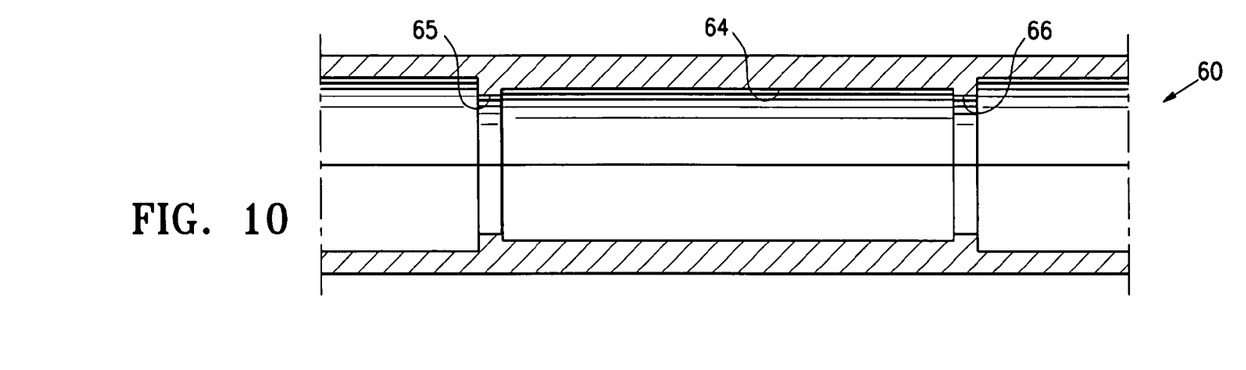
FIG. 10 illustrates a longitudinal cross sectional view of an alternative embodiment of a stepped inner diameter mold useful in a method of mounting a stent on a balloon catheter, in which end portions of the middle section of the mold have a smaller inner diameter than the portion of middle section therebetween.

FIG. 10 illustrates a longitudinal cross sectional view of an alternative radial restraining mold 60 with a stepped inner diameter, in which end portions 65, 66 of the middle section 64 of the mold have a smaller inner diameter than the portion of middle section 64 therebetween. The reduced inner diameter end portions 65, 66, cause the ends of the stent 30 to further embed down into the balloon during the stent mounting. Embedding the ends of the stent to a greater degree than a central section of the stent improves stent retention and advanceability of the system.

Figure 11:
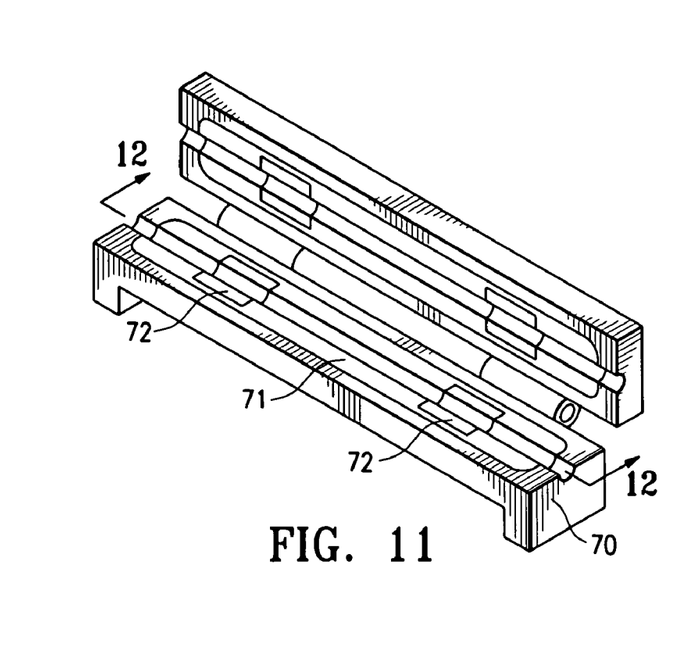
FIG. 11 is an isometric view of an alternative mold useful in a method embodying features of the invention, having an insulating non-metal body portion and a metal body portion.

In a presently preferred embodiment, the mold 10/50/60 is formed of metal, so that the metallic body of the mold defines the entire length of the bore that receives the balloon, and defines an outer surface of the mold. The metallic body substantially uniformly heats the entire length of the balloon within the mold. In an alternative embodiment, the mold selectively heats sections of the balloon within the bore of the mold (i.e., the mold has sections which differentially conduct heat). For example, FIG. 11 illustrates an isometric view of an alternative radial restraining mold 70, having a body 71 formed of an insulating material such as a plastic with metal portions 72, which allows for selective heating of the balloon portion of a catheter. The metal portions 72 are heat conducting, and the insulating (e.g., plastic) body 71 is not heat conducting, or at least is substantially less heat conducting than the metal portions. For example, when a metal portion was heated to 163° F. (73° C.), the maximum temperature measured in the adjacent insulating plastic portion was 109° F. (43° C.). As a result, the balloon portion proximal and distal to the stent can be placed at the metal portions 72, with the balloon central working length section (having the stent thereon) located between the metal portions 72, so that the plastic of the mold body insulates the working length section of the balloon portion from the elevated temperatures used during the stent mounting.

Insulating at least the central working length section of the balloon portion from heat protects the drug delivery coating of the stent from damage during the stent mounting procedure. Depending on the length of the metal portions 72, the plastic body 71 typically also insulates the balloon skirt sections (secured to the shaft) from heat of the heat transfer medium during the stent mounting procedure.

In a presently preferred embodiment, the insulating material forming the mold body 71 is a plastic such as polyetheretherketone (PEEK), or a machinable polyimide such as Vespel, although non-plastic insulating materials can alternatively be used such as ceramics including Macor (a machinable glass ceramic).

Figure 12:
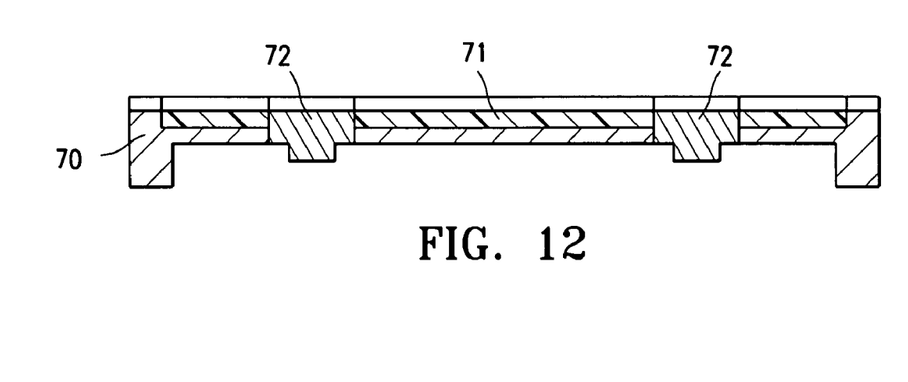
FIG. 12 illustrates a longitudinal cross sectional view of the mold bottom half of FIG. 11, taken along line 12-12.

FIG. 12 illustrates a longitudinal cross sectional view of the bottom half of the mold 70 of FIG. 11, taken along line 12-12. In a presently preferred embodiment, the metal portions 72 have, along at least a section thereof, a larger wall thickness (from the inner to the outer surface) than the adjacent sections of the plastic body 71 so that the metal portions 72 have at least a section which protrudes from the outer surface of the plastic body 71. The heating platens (discussed above in relation to the embodiment of FIG. 3) will therefore contact the protruding outer surface of the metal portions 72 without contacting the plastic body 71 during the stent mounting procedure. The air gap between the heating platens and the plastic body 71 sections will further reduce heat transfer to the drug delivery layer of a stent within the mold 70. In the illustrated embodiment, the plastic body 71, which together with the metal portions 72 defines the length of the bore receiving the balloon, is within an outer housing, typically formed of a metal, which surrounds the outer surfaces of the plastic body. The illustrated metal portions 72 have a section with a sufficiently large wall thickness such that the metal portions 72 protrude from the outer surface of the outer housing.

Figure 13:
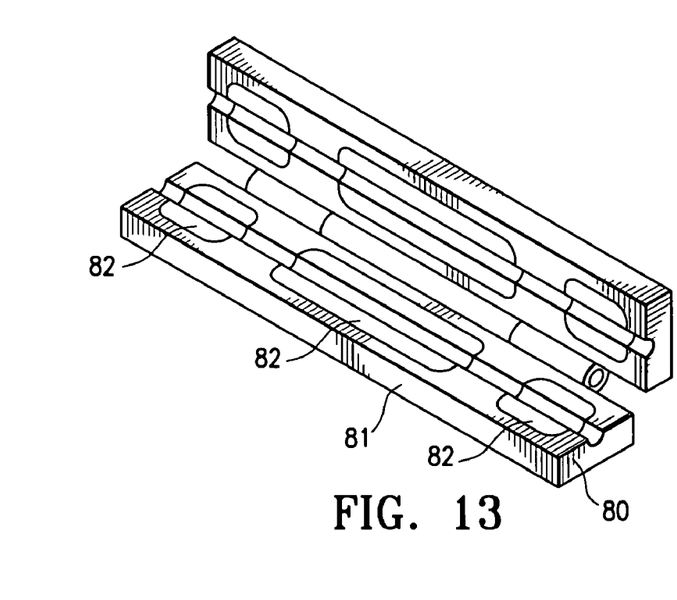
FIG. 13 is an isometric view of an alternative partially insulating mold useful in a method embodying features of the invention, having a metallic body with insulating non-metal inserts.

FIG. 13 illustrates an isometric view of an alternative embodiment of a selective heating mold 80 which embodies features of the invention, having a metallic body 81 with insulating plastic inserts 82. In the illustrated embodiment, three plastic inserts 82 are present, positioned at sections of the mold configured to receive the central working length section of balloon, and the skirt sections of the balloon secured to the shaft. The sections of the metallic body 81 of the mold located between the adjacent plastic inserts 82 are configured to receive the inflatable conical sections of the balloon (i.e., the balloon sections which extend between the central working length and the skirt sections of the balloon). The plastic inserts 82 preferably have a wall thickness which is less than the wall thickness of the metallic body 81. As a result, the metallic body 81 preferably defines the outer surface of the mold along the entire length thereof, and the metallic body 81 together with the plastic inserts 82 define sections of the bore of the mold. Alternatively, the wall thickness of the plastic inserts is equal to the wall thickness of the metallic body, so that the metallic body together with the plastic inserts define sections of the outer surface of the mold 80.

The dimensions of the stent delivery balloon catheter 20, 40 are determined largely by the size of the balloon and guidewire to be employed, the catheter type, and the size of the artery or other body lumen through which the catheter must pass or the size of the stent being delivered. Typically, the outer tubular member 24 has an outer diameter of about 0.025 to about 0.04 inch (0.064 to 0.10 cm), usually about 0.037 inch (0.094 cm), and the wall thickness of the outer tubular member 24 can vary from about 0.002 to about 0.008 inch (0.0051 to 0.02 cm), typically about 0.003 to 0.005 inch (0.0076 to 0.013 cm). The inner tubular member 26 typically has an inner diameter of about 0.01 to about 0.018 inch (0.025 to 0.046 cm), usually about 0.016 inch (0.04 cm), and a wall thickness of about 0.004 to about 0.008 inch (0.01 to 0.02 cm). The overall length of the catheter 20, 40 may range from about 100 to about 150 cm, and is typically about 143 cm. Preferably, balloon 22, 42 has a length of about 0.8 cm to about 6 cm, and an inflated working diameter of about 2 mm to about 10 mm.

Inner tubular member 26 and outer tubular member 24 can be formed by conventional techniques, for example by extruding and necking materials already found useful in intravascular catheters such a polyethylene, polyvinyl chloride, polyesters, polyamides, polyimides, polyurethanes, and composite materials. The various components may be joined using conventional bonding methods such as by fusion bonding or use of adhesives. Although the shaft is illustrated as having an inner and outer tubular member, a variety of suitable shaft configurations may be used including a dual lumen extruded shaft having a side-by-side lumens extruded therein. Similarly, although the embodiment illustrated in FIG. 6 is an over-the-wire type balloon catheter, the catheter of this invention may comprise a variety of intravascular catheters, such as rapid exchange type balloon catheters. Rapid exchange catheters generally comprise a shaft having a relatively short guidewire lumen extending from a guidewire distal port at the catheter distal end to a guidewire proximal port spaced a relatively short distance from the distal end of the catheter and a relatively large distance from the proximal end of the catheter.

While the present invention is described herein in terms of certain preferred embodiments, those skilled in the art will recognize that various modifications and improvements may be made to the invention without departing from the scope thereof. For example, while discussed primarily in terms of a drug delivery stent, aspects of the invention may be useful with an alternative prosthesis or stent (e.g., a bare metal stent). Moreover, although individual features of one embodiment of the invention may be discussed herein or shown in the drawings of the one embodiment and not in other embodiments, it should be apparent that individual features of one embodiment may be combined with one or more features of another embodiment or features from a plurality of embodiments.

What is claimed:

1. A method of mounting a drug delivery stent on a balloon catheter, comprising:
   a) positioning a drug delivery stent on a balloon of a balloon catheter, the stent having a drug delivery layer and an outer diameter;
   b) positioning the balloon with the drug delivery stent thereon within a polished bore of a mold, the mold having a metallic wall with a polished inner surface defining the mold bore, the bore having an inner diameter wherein such inner diameter corresponds to the outer diameter of the stent; and
   c) pressurizing and heating the balloon within the mold, to mount the stent on the balloon without damaging the drug delivery layer of the stent, wherein the balloon is heated by heating the mold by contacting a surface of the mold with a conductive heating element member which heats the mold purely by conduction and which provides temperature control to the mold with a tolerance of about ±1 degree to about ±2 degrees F.

2. The method of claim 1 wherein the conductive heating element member comprises a metal platen, and heating the mold comprises pressing the platen against an outer surface of the mold.

3. The method of claim 1 wherein the conductive heating element member has a length which is at least as long as an inflatable section of the balloon, and the conductive heating element member is brought into contact with a length of the mold corresponding to the location of the drug delivery stent therein.

4. A method of mounting a drug delivery stent on a balloon catheter, comprising:
   a) positioning a drug delivery stent on a balloon of a balloon catheter, the stent having a drug delivery layer, and an outer diameter;
   b) positioning the balloon with the drug delivery stent thereon within a polished bore of a mold formed at least in part of a metallic material, the bore having an inner diameter, wherein such inner diameter corresponds to the outer diameter of the stent; and
   c) pressurizing and heating the balloon within the mold, to mount the stent on the balloon without damaging the drug delivery layer of the stent, wherein the balloon is heated by heating the mold with a heat transfer medium which provides temperature control to the mold with a tolerance of about ±1 degree to about ±2 degrees F.

5. The method of claim 4 wherein the heat transfer medium has a relatively high thermal conductivity higher than that of air, and heating the mold comprises submerging the mold in a liquid bath, or contacting a surface of the mold with a conductive heating element member.

6. The method of claim 4 wherein heating the mold comprises contacting a surface of the mold with a conductive heating element member.

7. The method of claim 4 wherein heating the mold comprises submerging the mold in a liquid bath, and the mold is configured to seal the bore of the mold, so that the mold is submerged without liquid or humidity from the liquid bath contacting the drug delivery stent within the mold.

8. The method of claim 4 wherein the drug of the drug delivery layer of the stent has a thermal limit, and the balloon is heated to an elevated temperature which is significantly less than the thermal limit of the drug.

9. The method of claim 4 wherein the bore is defined by a polished inner surface having a polish finish equal to or smaller than about 0.4 microns, and wherein c) comprises radially restraining the drug delivery stent on the pressurized and heated balloon within the bore of the mold such that the drug delivery stent contacts the polished inner surface of the mold.

10. The method of claim 4 wherein the mold is split-mold with hinged halves, and including removing the balloon catheter with the drug delivery stent mounted thereon from the mold by opening the mold halves at the mold hinge.

11. The method of claim 4 wherein pressurizing the balloon to mount the drug delivery stent on the balloon expands the balloon without increasing the diameter of the bore, to at least partially embed the drug delivery stent in an outer surface of the balloon and control the outer diameter of the mounted stent on the balloon.

12. The method of claim 4 wherein the mold bore has a stepped inner diameter comprising enlarged inner diameter sections on either end of a middle section, so that mounting the drug delivery stent on the balloon forms shoulders in the balloon adjacent ends of the stent with an outer diameter greater than an outer diameter of the unexpanded stent mounted on the balloon.

13. The method of claim 12 wherein the middle section of the mold bore has reduced inner diameter end portions, so that mounting the drug delivery stent on the balloon causes ends of the stent to be more embedded than a central section of the stent.

14. The method of claim 4 wherein the mold has a metallic body defining the bore and an outer surface of the mold, so that heating the mold substantially uniformly heats the entire length of the balloon within the bore of the mold.

15. The method of claim 4 wherein the mold has a body with a heat conducting metallic section and an insulating non-metal section, so that heating the mold selectively heats sections of the balloon within the bore of the mold.

16. The method of claim 15 wherein the mold body is a non-metal material with two heat conducting metal sections spaced apart to define a region of the bore therebetween configured to receive the drug delivery stent, so that heating the mold selectively heats the sections of the balloon on either end of the stent to a higher temperature than the section of the balloon having the stent thereon.

17. The method of claim 16 wherein the two heat conducting metal sections protrude from the outer surface of the plastic body so that heating the mold comprises contacting the protruding outer surface of the two heat conducting metal sections with a conductive heating element member without contacting the plastic body of the mold.

18. The method of claim 15 wherein the mold body is metal with the insulating non-metal portion defining at least a region of the bore configured to receive the drug delivery stent, so that heating the mold selectively heats the sections of the balloon on either end of the stent to a higher temperature than the section of the balloon having the stent thereon.

19. A method of mounting a stent on a catheter balloon, comprising:
   a) positioning a stent on a balloon catheter, the balloon catheter having an elongated shaft with an inflation lumen and a guidewire lumen and an inflatable balloon on a distal shaft section with an interior in fluid communication with the inflation lumen, and the stent having an open-walled body of stent struts with gaps between adjacent stent struts;
   b) applying a radially compressive force on an outer surface of the stent and thereby decreasing the outer diameter of the stent on the balloon catheter;
   c) heating the balloon and introducing inflation media into the interior of the balloon to radially expand the balloon with the stent restrained from radially expanding by a mold around an outer surface of the stent, so that the balloon expands into the stent gaps to embed the stent in an outer surface of the balloon, wherein such mold has a section with an inner diameter that corresponds to the decreased diameter of the stent, to thereby mount the stent on the balloon, wherein the mold has a stepped inner diameter so that expanding the balloon forms a shoulder in the balloon adjacent an end of the stent with an outer diameter greater than an outer diameter of the mounted stent in an unexpanded configuration; and
   d) removing the inflation media from the balloon interior.

20. The method of claim 19 wherein the mold inner chamber has enlarged inner diameter sections on either end of a middle section, and the middle section has reduced inner diameter end portions, so that expanding the balloon causes ends of the stent to be more embedded than a central section of the stent.

* * * * *

UNITED STATES PATENT AND TRADEMARK OFFICE
CERTIFICATE OF CORRECTION

| | | |
|---|---|---|
| PATENT NO. | : 7,563,400 B2 | Page 1 of 1 |
| APPLICATION NO. | : 11/105085 | |
| DATED | : July 21, 2009 | |
| INVENTOR(S) | : Bruce Wilson et al. | |

It is certified that error appears in the above-identified patent and that said Letters Patent is hereby corrected as shown below:

Title Page, Item (56) References Cited, U.S. Patent Documents, page 2, insert --4,081,092 7/1978 Cho et al.--.

Signed and Sealed this

Eighth Day of March, 2011

David J. Kappos
*Director of the United States Patent and Trademark Office*